(12) United States Patent
Aster et al.

(10) Patent No.: US 8,178,546 B2
(45) Date of Patent: May 15, 2012

(54) DIARYLTRIAZOLES AS INHIBITORS OF 11-BETA-HYDROXYSTEROID DEHYDROGENASE-1

(75) Inventors: Susan D. Aster, Teaneck, NJ (US); James M. Balkovec, Martinsville, NJ (US); Donald W. Graham, Mountainside, NJ (US); Xin Gu, Scotch Plains, NJ (US); Nancy J. Kevin, East Brunswick, NJ (US); Gool F. Patel, Califon, NJ (US); Mitree Ponpipom, Branchburg, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 220 days.

(21) Appl. No.: 12/759,737

(22) Filed: Apr. 14, 2010

(65) Prior Publication Data
US 2010/0256387 A1    Oct. 7, 2010

Related U.S. Application Data

(62) Division of application No. 10/593,010, filed on Sep. 18, 2006, now abandoned.

(51) Int. Cl.
*C07D 249/08* (2006.01)
(52) U.S. Cl. .................................................. 514/266.4
(58) Field of Classification Search ............... 514/266.4
See application file for complete search history.

(56) References Cited

U.S. PATENT DOCUMENTS
2005/0070720 A1 * 3/2005 Balkovec et al. ......... 548/263.2

FOREIGN PATENT DOCUMENTS
GB   1571481   7/1980
JP   08-12657   1/1996

OTHER PUBLICATIONS

Gautun, "Regioselectivity in the thermal rearrangement of unsymmetrical . . . ", Molecules (2001), vol. 6, pp. 969-978.
Neugebauer, "2,5-Dihydro-1h-1,2,4-triazol-2-yl radicals: . . . ", Tetrahedron (1995), vol. 51, pp. 12883-12898.
Aster, "Bis-aryl triazoles as selective inhibitors of 11beta-hydroxysteroid . . . ", Bioorg. & Med. Chem. Letters (2008), vol. 18, pp. 2799-2804.
Dorwald, "Side Reactions in Organic Synthesis: A guide to successful synthesis design", Wiley-VCH Verlag GambH & Co. KGaA (2005), Preface, p. ix.
Seckl, "Minireview: 11beta-hydroxysteroid dehydrogenase Type 1—. . . ", Endocrinology (2001), vol. 142, pp. 1371-1376.
Hermanowski-Vosatka, "11beta-HSD1 inhibition ameliorates metabolic syndrome . . . ", J. Exp. Med. (2005), vol. 202, pp. 517-527.
Brunn, "1,3-Dipolare cycloadditionen: Cycloadditionen von N-substituierten oxazolium—. . . ", Chem. Ber. (1971), vol. 104, pp. 1562-1572.

* cited by examiner

*Primary Examiner* — Brandon Fetterolf
*Assistant Examiner* — Paul Zarek
(74) *Attorney, Agent, or Firm* — Richard S. Parr; Catherine D. Fitch

(57) ABSTRACT

2,5-Diaryl-1,2,4-triazole derivatives of structural formula I are selective inhibitors of the 11β-hydroxysteroid dehydrogenase Type 1 enzyme (11β-HSD-1). The compounds are useful for the treatment of diabetes, hyperglycemia, obesity, insulin resistance, atherosclerosis, dyslipidemia, hyperlipidemia, hypertension, and Metabolic Syndrome. Also disclosed are novel compounds of structural formula II which are inhibitors of 11β-HSD-1.

5 Claims, No Drawings

DIARYLTRIAZOLES AS INHIBITORS OF 11-BETA-HYDROXYSTEROID DEHYDROGENASE-1

FIELD OF THE INVENTION

The present invention relates to 3,5-diaryl-1,2,4-triazoles as inhibitors of the enzyme 11-beta-hydroxysteroid dehydrogenase Type I (11β-HSD-1) which are useful for the treatment, control, or prevention of disorders, diseases, and conditions responsive to inhibition of 11β-HSD-1, including diabetes, insulin resistance, obesity, lipid disorders, atherosclerosis, hypertension, and other diseases and conditions, such as Metabolic Syndrome.

BACKGROUND OF THE INVENTION

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with Type 2 diabetes, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension and alterations in lipid, lipoprotein and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension is critically important in the clinical management and treatment of diabetes mellitus.

Many patients who have insulin resistance but have not developed Type 2 diabetes are also at a risk of developing symptoms referred to as "Syndrome X" or "Metabolic Syndrome". Syndrome X or Metabolic Syndrome is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

Treatment of Type 2 diabetes typically includes physical exercise and dieting. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate insulin-resistant tissues. However, dangerously low levels of plasma glucose can result, and an increased level of insulin resistance can ultimately occur.

Biguanides increase insulin sensitivity, resulting in some correction of hyperglycemia. However, many biguanides, e.g., phenformin and metformin, cause lactic acidosis, nausea and diarrhea.

The glitazones (i.e. 5-benzylthiazolidine-2,4-diones) form a newer class of compounds with the potential for ameliorating hyperglycemia and other symptoms of Type 2 diabetes. These agents substantially increase insulin sensitivity in muscle, liver and adipose tissue, resulting in partial or complete correction of the elevated plasma levels of glucose substantially without causing hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes. For a review of insulin-sensitizing agents and other mechanisms for the treatment of Type 2 diabetes, see M. Tadayyon and S. A. Smith, "Insulin sensitisation in the treatment of Type 2 diabetes," *Expert Opin. Investig. Drugs,* 12: 307-324 (2003).

There is a continuing need for new methods of treating diabetes and related conditions, such as Metabolic Syndrome. The present invention meets this and other needs.

SUMMARY OF THE INVENTION

The present invention provides a method for inhibiting 11β-hydroxysteroid dehydrogenase Type 1 (11β-HSD-1) with a compound of structural formula I:

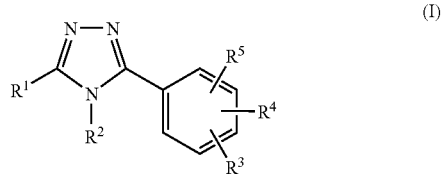

Compounds of formula I are useful for the treatment, control or prevention of disorders, diseases, and conditions responsive to the inhibition of 11β-HSD-1, such as insulin resistance, Type 2 diabetes, a lipid disorder, obesity, atherosclerosis, hypertension, and Metabolic Syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of 11β-HSD-1 in a subject in need thereof by administering the compounds and pharmaceutical compositions of the present invention.

The present invention also relates to methods for the treatment or control of Type 2 diabetes, obesity, a lipid disorder, atherosclerosis, hypertension, and Metabolic Syndrome by administering the compounds and pharmaceutical compositions of the present invention.

The present invention also relates to methods for treating obesity by administering the compounds of the present invention in combination with a therapeutically effective amount of another agent known to be useful to treat the condition.

The present invention also relates to methods for treating Type 2 diabetes by administering the compounds of the present invention in combination with a therapeutically effective amount of another agent known to be useful to treat the condition.

The present invention also relates to methods for treating atherosclerosis by administering the compounds of the present invention in combination with a therapeutically effective amount of another agent known to be useful to treat the condition.

The present invention also relates to methods for treating a lipid disorder by administering the compounds of the present invention in combination with a therapeutically effective amount of another agent known to be useful to treat the condition.

The present invention also relates to methods for treating Metabolic Syndrome by administering the compounds of the present invention in combination with a therapeutically effective amount of another agent known to be useful to treat the condition.

The present invention also relates to the use of a compound of structural formula I, or a pharmaceutically acceptable salt thereof, for the manufacture of a medicament for use in the treatment, prevention, or control of clinical conditions, in a mammal in need thereof, for which an inhibitor of 11β-HSD-1 is indicated. Such clinical conditions include insulin resistance, Type 2 diabetes, a lipid disorder, obesity, atherosclerosis, hypertension, and Metabolic Syndrome.

The present invention also provides novel compounds which are useful as inhibitors of 11β-HSD-1.

DETAILED DESCRIPTION OF THE INVENTION

The present invention is concerned with a method for the treatment, control, or prevention of disorders, diseases, and conditions responsive to inhibition of 11β-HSD-1 in a mammal in need thereof comprising administering to the mammal a therapeutically effective amount of a compound of structural formula I:

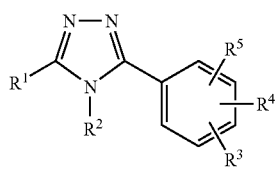

(I)

or a pharmaceutically acceptable salt thereof; wherein
each n is 0, 1, or 2;
each p is 0, 1, or 2;
$R^1$ is aryl or heteroaryl wherein heteroaryl is selected from the group consisting of
  pyridyl,
  thienyl,
  furyl,
  pyrazolyl,
  thiazolyl,
  oxazolyl,
  imidazolyl,
  indolyl,
  benzothiophenyl,
  benzofuryl, and
  benzimidazolyl;
in which aryl and heteroaryl are substituted with one to four substituents independently selected from $R^3$, $R^4$, and $R^5$;
$R^2$ is selected from the group consisting of
  $C_{1-4}$ alkyl,
  $C_{2-4}$ alkenyl, and
  $(CH_2)_n$—$C_{3-6}$ cycloalkyl;
$R^3$, $R^4$, and $R^5$ are each independently selected from the group consisting of
  hydrogen,
  formyl,
  $C_{1-6}$ alkyl,
  $C_{2-6}$ alkenyl,
  $(CH_2)_n$-aryl,
  $(CH_2)_n$-heteroaryl,
  $(CH_2)_n$-heterocyclyl,
  $(CH_2)_n C_{3-7}$ cycloalkyl,
  halogen,
  $OR^7$,
  $(CH_2)_n N(R^7)_2$,
  cyano,
  $(CH_2)_n CO_2 R^7$,
  $NO_2$,
  $(CH_2)_n NR^7 SO_2 R^6$,
  $(CH_2)_n SO_2 N(R^7)_2$,
  $(CH_2)_n S(O)_p R^6$,
  $(CH_2)_n SO_2 OR^7$,
  $(CH_2)_n NR^7 C(O)N(R^7)_2$,
  $(CH_2)_n C(O)N(R^7)_2$,
  $(CH_2)_n NR^6 C(O)R^6$,
  $(CH_2)_n NR^6 CO_2 R^7$,
  $O(CH_2)_n C(O)N(R^7)_2$,
  $CF_3$,
  $CH_2 CF_3$,
  $OCF_3$,
  $OCHCF_2$, and
  $OCH_2 CF_3$;
wherein aryl, heteroaryl, cycloalkyl, and heterocyclyl are unsubstituted or substituted with one to three substituents independently selected from halogen, hydroxy, C1-4 alkyl, trifluoromethyl, trifluoromethoxy, and C1-4 alkoxy; and wherein any methylene (CH2) carbon atom in R3, R4, and R5 is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;
each $R^6$ is independently selected from the group consisting of
  $C_{1-8}$ alkyl,
  $C_{2-4}$ alkynyl,
  $(CH_2)_n$-aryl,
  $(CH_2)_n$-heteroaryl, and
  $(CH_2)_n C_{3-7}$ cycloalkyl;
wherein alkyl and cycloalkyl are unsubstituted or substituted with one to five substituents independently selected from halogen, oxo, $C_{1-4}$ alkoxy, $C_{1-4}$ alkylthio, hydroxy, and amino; and aryl and heteroaryl are unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy;

or two $R^6$ groups together with the atom to which they are attached form a 5- to 8-membered mono- or bicyclic ring system optionally containing an additional heteroatom selected from O, S, and $NC_{0-4}$ alkyl; and each $R^7$ is hydrogen or $R^6$.

In one embodiment of the compounds of formula I, $R^2$ is methyl.

In a second embodiment of the compounds of formula I, $R^3$ is hydrogen and $R^4$ and $R^5$ are each independently selected from the group consisting of amino, halogen, hydroxy, nitro, trifluoromethyl, trifluoromethoxy, difluoromethoxy, $C_{2-3}$ alkynyloxy, $C_{1-5}$ alkyl, cyclopropyl, $C_{1-4}$ alkoxy, $C_{1-4}$ alkylthio, and $C_{1-4}$ alkylsulfonyl.

In a third embodiment of the compounds of formula I, $R^1$ is phenyl or naphthyl each of which is substituted with one to three substituents independently selected from $R^3$. In a class of this embodiment, $R^3$ is selected from the group consisting of amino, halogen, hydroxy, nitro, trifluoromethyl, trifluoromethoxy, difluoromethoxy, $C_{1-5}$ alkyl, $C_{1-4}$ alkoxy, $C_{1-4}$ alkylsulfonyl, phenyl, phenyloxy, phenylthio, and phenylsulfonyl, wherein the phenyl moiety of each is unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy. In a subclass of this class, $R^2$ is methyl.

In a fourth embodiment of the compounds of formula I, R1 is heteroaryl substituted with one to three substituents independently selected from R3. In a class of this embodiment, R2 is methyl. In a second class of this embodiment, heteroaryl is pyrazolyl or indolyl, each of which is substituted with one to three substituents independently selected from R3. In a subclass of this second class, R2 methyl.

In another subclass of this second class, R3 is selected from the group consisting of amino, halogen, hydroxy, nitro, trifluoromethyl, trifluoromethoxy, difluoromethoxy, C1-5 alkyl, C1-4 alkoxy, C1-4 alkylsulfonyl, phenyl, phenyloxy, phenylthio, and phenylsulfonyl, wherein the phenyl moiety of each is unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy. In another subclass of this subclass, $R^2$ is methyl.

Illustrative, but nonlimiting examples, of compounds of Formula I that are useful in the methods of the present invention are the following:

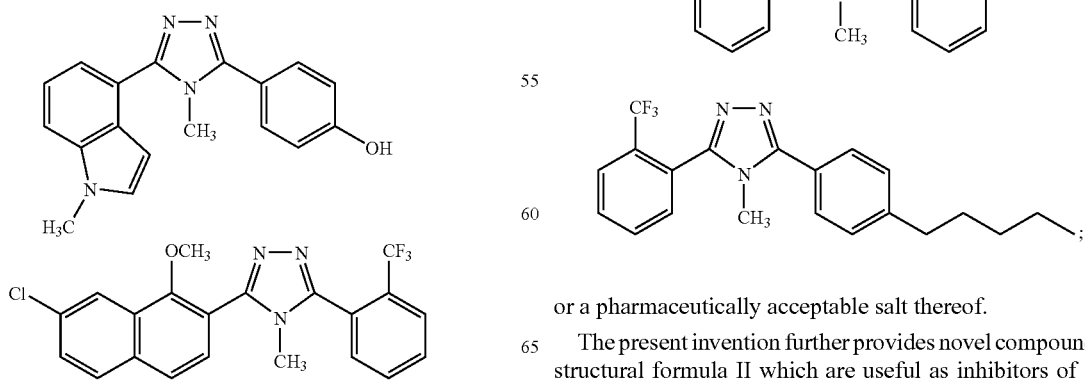

or a pharmaceutically acceptable salt thereof.

The present invention further provides novel compounds of structural formula II which are useful as inhibitors of 11β-HSD-1:

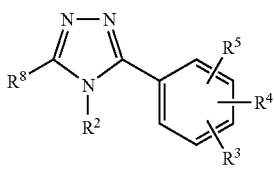

(II)

or a pharmaceutically acceptable salt thereof; wherein
each n is 0, 1, or 2;
each p is 0, 1, or 2;
$R^8$ is naphthyl or heteroaryl wherein heteroaryl is selected from the group consisting of
pyridyl,
thienyl,
furyl,
pyrazolyl,
thiazolyl,
oxazolyl,
imidazolyl,
indolyl,
benzothiophenyl,
benzofuryl, and
benzimidazolyl;
in which naphthyl and heteroaryl are substituted with one to three substituents independently selected from $R^3$;
$R^2$ is methyl or cyclopropyl;
$R^3$, $R^4$, and $R^5$ are each independently selected from the group consisting of
hydrogen,
formyl,
$C_{1-6}$ alkyl,
$C_{2-6}$ alkenyl,
$(CH_2)_n$-aryl,
$(CH_2)_n$-heteroaryl,
$(CH_2)_n$-heterocyclyl,
$(CH_2)_n C_{3-7}$ cycloalkyl,
halogen,
$OR^7$,
$(CH_2)_n N(R^7)_2$,
cyano,
$(CH_2)_n CO_2 R^7$,
$NO_2$,
$(CH_2)_n NR^7 SO_2 R^6$,
$(CH_2)_n SO_2 N(R^7)_2$,
$(CH_2)_n S(O)_p R^6$,
$(CH_2)_n SO_2 OR^7$,
$(CH_2)_n NR^7 C(O)N(R^7)_2$,
$(CH_2)_n C(O)N(R^7)_2$,
$(CH_2)_n NR^6 C(O)R^6$,
$(CH_2)_n NR^6 CO_2 R^7$,
$O(CH_2)_n C(O)N(R^7)_2$,
$CF_3$,
$CH_2 CF_3$,
$OCF_3$,
$OCHCF_2$, and
$OCH_2 CF_3$;
wherein aryl, heteroaryl, cycloalkyl, and heterocyclyl are unsubstituted or substituted with one to three substituents independently selected from halogen, hydroxy, $C_{1-4}$ alkyl, trifluoromethyl, trifluoromethoxy, and $C_{1-4}$ alkoxy; and
wherein any methylene ($CH_2$) carbon atom in $R^3$, $R^4$, and $R^5$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;
each $R^6$ is independently selected from the group consisting of
$C_{1-8}$ alkyl,
$(CH_2)_n$-aryl,
$(CH_2)_n$-heteroaryl, and
$(CH_2)_n C_{3-7}$ cycloalkyl;
wherein alkyl and cycloalkyl are unsubstituted or substituted with one to five substituents independently selected from halogen, oxo, $C_{1-4}$ alkoxy, $C_{1-4}$ alkylthio, hydroxy, amino; and aryl and heteroaryl are unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy;
or two $R^6$ groups together with the atom to which they are attached form a 5- to 8-membered mono- or bicyclic ring system optionally containing an additional heteroatom selected from O, S, and $NC_{1-4}$ alkyl; and
each $R^7$ is hydrogen or $R^6$.

In one embodiment of the novel compounds of formula II, $R^2$ is methyl.

In a second embodiment of the novel compounds of the present invention, $R^8$ is indolyl or pyrazolyl substituted with one to three substituents independently selected from $R^3$ as defined above. In a class of this embodiment, $R^2$ is methyl.

Illustrative of the novel compounds of the present invention are the following:
4-methyl-3,5-bis[2-(trifluoromethyl)phenyl]-4H-1,2,4-triazole;
4-methyl-3-[4-(methylthio)-2-(trifluoromethyl)phenyl]-5-[2-(trifluoromethyl)phenyl]-4H-1,2,4-triazole;
4-methyl-3-(4-pentylphenyl)-5-[2-(trifluoromethyl)phenyl]-4H-1,2,4-triazole;
3-(2-chlorophenyl)-4-methyl-5-[2-(trifluoromethyl)phenyl]-4H-1,2,4-triazole;
3-(1-methoxy-2-naphthyl)-4-methyl-5-[2-(trifluoromethyl)phenyl]-4H-1,2,4-triazole;
4-[5-(2-chlorophenyl)-4-methyl-4H-1,2,4-triazol-3-yl]-1-methyl-1H-indole;
4-{4-methyl-5-[2-(trifluoromethyl)phenyl]-4H-1,2,4-triazol-3-yl}-1-methyl-1H-indole;
3-(2-bromophenyl)-4-methyl-5-[2-(trifluoromethyl)phenyl]-4H-1,2,4-triazole;
3-(7-chloro-1-methoxy-2-naphthyl)-4-methyl-5-[2-(trifluoromethyl)-4H-1,2,4-triazole;
4-[4-methyl-5-(1-methyl-1H-indol-4-yl)-4H-1,2,4-triazol-3-yl]phenol;
3-(2,4-dichlorophenyl)-4-methyl-5-[2-(trifluoromethyl)phenyl]-4H-1,2,4-triazole;
3-[2,4-bis(trifluoromethyl)phenyl]-4-methyl-5-[2-(trifluoromethyl)phenyl]-4H-1,2,4-triazole;
3-(2-chlorophenyl)-5-(2,4-dichlorophenyl)-4-methyl-4H-1,2,4-triazole;
3-(2-chloro-4-fluorophenyl)-4-methyl-5-[2-(trifluoromethyl)phenyl]-4H-1,2,4-triazole;
3-(2,4-dichlorophenyl)-4-methyl-5-[2-(methylthio)phenyl]-4H-1,2,4-triazole;
3-(2,4-dichlorophenyl)-4-methyl-5-(2-methylphenyl)-4H-1,2,4-triazole;
3-(2-chlorophenyl)-5-[5-(2-chlorophenyl)-1-methyl-1H-pyrazol-3-yl]-4-methyl-4H-1,2,4-triazole;
4-[5-(2-methoxyphenyl)-4-methyl-4H-1,2,4-triazol-3-yl]-1-methyl-1H-indole;
4-methyl-3-(2-methyl-1-naphthyl)-5-[2-(trifluoromethyl)phenyl]-4-methyl-4H-1,2,4-triazole;

3-(1,4-dichloro-2-naphthyl)-4-methyl-5-[2-(trifluoromethyl)phenyl]-4H-1,2,4-triazole;
3-(4-chloro-1-methoxy-2-naphthyl)-4-methyl-5-[2-(trifluoromethyl)phenyl]-4H-1,2,4-triazole;
3-(1-fluoro-2-naphthyl)-4-methyl-5-[2-(trifluoromethyl)phenyl]-4H-1,2,4-triazole;
N-methyl-2-{4-methyl-5-(trifluoromethyl)phenyl-4H-1,2,4-triazol-3-yl}naphthalen-1-amine;
3,5-bis-(2,4-dimethylphenyl)-4-methyl-4H-1,2,4-triazole;
3-(2,4-dichlorophenyl)-5-[2-(ethylthio)phenyl]-4-methyl-4H-1,2,4-triazole;
3-(2-cyclopropylphenyl)-5-(2,4-dichlorophenyl)-4-methyl-4H-1,2,4-triazole;
3-[(2-chloro-4-(ethylthio)phenyl)]-5-(2-fluorophenyl)-4-methyl-4H-1,2,4-triazole;
3-(2-methoxyphenyl)-4-methyl-5-[2-(trifluoromethyl)phenyl]-4H-1,2,4-triazole;
3-(2,6-dichlorophenyl)-4-methyl-5-[2-(trifluoromethyl)phenyl]-4H-1,2,4-triazole;
3-(2-chlorophenyl)-5-[(2-difluoromethoxy)phenyl]-4-methyl-4H-1,2,4-triazole;
3-(2-chloro-4-fluorophenyl)-5-(2-chlorophenyl)-4-methyl-4H-1,2,4-triazole;
3-(2,4-dichlorophenyl)-5-[(2-difluoromethoxy)phenyl]-4-methyl-4H-1,2,4-triazole;
4-methyl-3-(2-phenoxyphenyl)-5-[2-(trifluoromethyl)phenyl]-4H-1,2,4-triazole;
4-methyl-3-[2-(trifluoromethoxy)phenyl]-5-[2-(trifluoromethyl)phenyl]-4H-1,2,4-triazole;
4-methyl-3-[2-(prop-2-yn-1-yloxy)phenyl]-5-[2-(trifluoromethyl)phenyl]-4H-1,2,4-triazole;
3-{2-[(4-chlorophenyl)thio]phenyl}-4-methyl-5-[2-(trifluoromethyl)phenyl]-4H-1,2,4-triazole;
3-[2-(difluoromethoxy)phenyl]-4-methyl-5-[2-(trifluoromethyl)phenyl]-4H-1,2,4-triazole;
3-(2-ethoxyphenyl)-4-methyl-5-[2-(trifluoromethyl)phenyl]-4H-1,2,4-triazole;
4-methyl-3-(2-propoxyphenyl)-5-[2-(trifluoromethyl)phenyl]-4H-1,2,4-triazole;
3,5-bis(2-chlorophenyl)-4-methyl-4H-1,2,4-triazole;
3,5-bis(2,3-dichlorophenyl)-4-methyl-4H-1,2,4-triazole;
3-(3-chloro-2-naphthyl)-4-methyl-5-[2-(trifluoromethyl)phenyl]-4H-1,2,4-triazole;
3-(5-chloro-6-methoxy-1-naphthyl)-4-methyl-5-[2-(trifluoromethyl)phenyl]-4H-1,2,4-triazole;
3-[2-(4-chlorophenoxy)phenyl]-4-methyl-5-[2-(trifluoromethyl)phenyl]-4H-1,2,4-triazole;
3-[4-(4-chlorophenoxy)phenyl]-4-methyl-5-[2-(trifluoromethyl)phenyl]-4H-1,2,4-triazole;
3-[4-chloro-5-(2-chlorophenyl)-1-methyl-1H-pyrazol-3-yl]-4-methyl-5-[2-(trifluoromethyl)phenyl]-4H-1,2,4-triazole;
4-methyl-3-(2,4,6-trichloro-1-naphthyl)-5-[2-(trifluoromethyl)phenyl]-4H-1,2,4-triazole;
3-(2-chlorophenyl)-4-methyl-5-[2-(trifluoromethoxy)phenyl]-4H-1,2,4-triazole;
3-(2-bromophenyl)-5-(2-methoxyphenyl)-4-methyl-4H-1,2,4-triazole;
3-(2,3-dichlorophenyl)-4-methyl-5-(2-methylphenyl)-4H-1,2,4-triazole;
3-(2,3-dichlorophenyl)-5-(2-methoxyphenyl)-4-methyl-4H-1,2,4-triazole;
3-(2-bromophenyl)-4-methyl-5-(2-methylphenyl)-4H-1,2,4-triazole;
4-methyl-3-(2-methylphenyl)-5-[2-(trifluoromethoxyl)phenyl]-4H-1,2,4-triazole;
3-(2-chlorophenyl)-4-cyclopropyl-5-[(2-(trifluoromethyl)phenyl]-4H-1,2,4-triazole;
3-(4-chloro-3-methoxy-2-naphthyl)-4-methyl-5-[(2-(methylthio)phenyl]-4H-1,2,4-triazole;
3-[2-(4-chlorophenoxy)phenyl]-4-methyl-5-[(2-(methylthio)phenyl]-4H-1,2,4-triazole;
3-[2-(4-chlorophenoxy)phenyl]-4-methyl-5-[(2-(methylsulfonyl)phenyl]-4H-1,2,4-triazole;
3-(2-chlorophenyl)-5-(2,3-dichlorophenyl)-4-methyl-4H-1,2,4-triazole;
3-(2-bromophenyl)-5-(2-chlorophenyl)-4-methyl-4H-1,2,4-triazole;
3-[2-(4-fluorophenoxy)phenyl]-4-methyl-5-[2-(trifluoromethyl)phenyl]-4H-1,2,4-triazole;
3-(2-chlorophenyl)-5-[2-chloro-3-(trifluoromethyl)phenyl]-4-methyl-4H-1,2,4-triazole; and
4-[4-methyl-5-(1,2,3-trimethyl-1H-indol-5-yl)-4H-1,2,4-triazol-3-yl]phenol;
or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include vinyl, allyl, isopropenyl, pentenyl, hexenyl, heptenyl, 1-propenyl, 2-butenyl, 2-methyl-2-butenyl, and the like. Where the specified number of carbon atoms permits, e.g., from $C_{5-10}$, the term alkenyl also includes cycloalkenyl groups, and combinations of linear, branched and cyclic structures. When no number of carbon atoms is specified, $C_{2-6}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl, and the like.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers, as well as mixtures thereof, are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

In a different aspect of the invention, a pharmaceutical composition is addressed comprising a compound in accordance with structural formula I, or a pharmaceutically acceptable salt or solvate thereof, in combination with a pharmaceutically acceptable carrier. By the term "solvate" is meant a hydrate, an alcoholate, or other solvate of crystallization.

In another aspect of the invention, a method of treating hyperglycemia, diabetes or insulin resistance in a mammalian patient in need of such treatment is addressed, which comprises administering to said patient an effective amount of a compound in accordance with structural formula I or a pharmaceutically salt or solvate thereof.

In another aspect of the invention, a method of treating Type 2 diabetes is disclosed in a mammalian patient in need of such treatment comprising administering to the patient an anti-diabetic effective amount of a compound in accordance with structural formula I.

In another aspect of the invention, a method of treating obesity in a mammalian patient in need of such treatment is disclosed comprising administering to said patient a compound in accordance with structural formula I in an amount that is effective to treat obesity.

In another aspect of the invention, a method of treating Metabolic Syndrome in a mammalian patient in need of such treatment is disclosed, comprising administering to said patient a compound in accordance with structural formula I in an amount that is effective to treat Metabolic Syndrome.

In another aspect of the invention, a method of treating a lipid disorder selected from the group consisting of dyslipidemia, hyperlipidemia, hypertriglyceridemia, hypercholesterolemia, low HDL, and high LDL in a mammalian patient in need of such treatment is disclosed, comprising administering to said patient a compound in accordance with structural formula I in an amount that is effective to treat said lipid disorder.

In another aspect of the invention, a method of treating atherosclerosis in a mammalian patient in need of such treatment is disclosed, comprising administering to said patient a compound in accordance with structural formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) a lipid disorder, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) a lipid disorder, (6) dyslipidemia, (7)

hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to delay the onset of said condition.

In another aspect of the invention, a method of reducing the risk of developing a condition selected from the group consisting of (1) hyperglycemia, (2) low glucose tolerance, (3) insulin resistance, (4) obesity, (5) a lipid disorder, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) a lipid disorder, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment, comprising administering to the patient an effective amount of a compound as defined in structural formula I and a compound selected from the group consisting of:

(a) dipeptidyl peptidase-IV (DP-IV) inhibitors;
(b) insulin sensitizing agents selected from the group consisting of (i) PPARγ agonists, (ii) PPARα agonists, (iii) PPARα/γ dual agonists, and (iv) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 analogs, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of (i) HMG-CoA reductase inhibitors, (ii) sequestrants, (iii) nicotinyl alcohol, nicotinic acid and salts thereof, (iv) inhibitors of cholesterol absorption, (v) acyl CoA:cholesterol acyltransferase inhibitors, and (vi) anti-oxidants;
(k) PPARδ agonists;
(l) antiobesity compounds;
(m) ileal bile acid transporter inhibitors;
(n) anti-inflammatory agents, excluding glucocorticoids;
(o) protein tyrosine phosphatase 1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents,* 11: 1677-1692 (2001)

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists, *Expert Opin. Ther. Patents,* 12: 1631-1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-Co A reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:
(1) a compound according to structural formula I,
(2) a compound selected from the group consisting of:
  (a) DP-IV inhibitors;
  (b) insulin sensitizing agents selected from the group consisting of (i) PPARγ agonists; (ii) PPARα agonists, (iii) PPARα/γ dual agonists, and (iv) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 analogs, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii) bile-acid sequestrants, (iii) nicotinyl alcohol, nicotinic acid or a salt thereof, (iv) inhibitors of cholesterol absorption, (v) acyl CoA:cholesterol acyltransferase inhibitors, and (vi) anti-oxidants;
  (k) PPARδ agonists;
  (l) antiobesity compounds;
  (m) ileal bile acid transporter inhibitors;
  (n) anti-inflammatory agents other than glucocorticoids;
  (o) protein tyrosine phosphatase 1B (PTP-1B) inhibitors; and
  (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and
(3) a pharmaceutically acceptable carrier.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of structural formula I are included in the present invention as well.

The compounds described herein are selective inhibitors of the 11β-HSD-1 enzyme. Thus, the present invention relates to the use of the 11β-HSD-1 inhibitors for inhibiting the reductase activity of 11β-hydroxysteroid dehydrogenase, which is responsible for the conversion of cortisone to cortisol. Excess cortisol is associated with numerous disorders, including Type 2 diabetes, obesity, dyslipidemia, insulin resistance and hypertension. Administration of the compounds of the present invention decreases the level of cortisol and other 11β-hydroxysteroids in target tissues, thereby reducing the effects of excessive amounts of cortisol and other 11β-hydroxysteroids. Inhibition of 11β-HSD-1 can be used to treat and control diseases mediated by abnormally high levels of cortisol and other 11β-hydroxysteroids, such as Type 2 diabetes, obesity, hypertension and dyslipidemia. Inhibition of 11β-HSD-1 activity in the brain such as to lower cortisol levels may also be useful to treat or reduce anxiety, depression, and cognitive impairment.

The present invention includes the use of an 11β-HSD-1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD-1 enzyme limits the conversion of cortisone, which is normally inert, to cortisol, which can cause or contribute to the symptoms of these diseases and conditions if present in excessive amounts.

Type 2 Diabetes and Hypertension:

The compounds of this invention are selective inhibitors of 11β-HSD-1 over 11β-HSD-2. While the inhibition of 11β-HSD-1 is useful for reducing cortisol levels and treating conditions related thereto, inhibition of 11β-HSD-2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing Type 2 diabetes in the presence of abnormally high levels of cortisol.

High levels of cortisol in tissues where the mineralocorticoid receptor is present often lead to hypertension Inhibition of 11β-HSD-1 shifts the ratio of cortisol and cortisone in specific tissues in favor of cortisone.

Administration of a therapeutically effective amount of an 11β-HSD-1 inhibitor is effective in treating, controlling, and ameliorating the symptoms of Type 2 diabetes, and administration of a therapeutically effective amount of an 11β-HSD-1 inhibitor on a regular basis delays or prevents the onset of Type 2 diabetes, particularly in humans.

Cushing's Syndrome:

The effect of elevated levels of cortisol is also observed in patients who have Cushing's Syndrome, which is a metabolic disease characterized by high levels of cortisol in the blood stream. Patients with Cushing's Syndrome often develop Type 2 diabetes.

Obesity, Metabolic Syndrome, Dyslipidemia:

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Metabolic Syndrome, such as high blood pressure, elevated VLDL and reduced HDL. Montague et al., Diabetes, 2000, 49: 883-888. Thus, the administration of an effective amount of an 11β-HSD-1 inhibitor is useful in the treatment or control of obesity. Long-term treatment with an 11β-HSD-1 inhibitor is also useful in delaying or preventing the onset of obesity, especially if the patient uses an 11β-HSD-1 inhibitor in combination with controlled diet and exercise.

By reducing insulin resistance and maintaining serum glucose at normal concentrations, compounds of the present invention also have utility in the treatment and prevention of conditions that accompany Type 2 diabetes and insulin resistance, including the Metabolic Syndrome or Syndrome X, obesity, reactive hypoglycemia and diabetic dyslipidemia.

Cognition and Dementia:

Excessive levels of cortisol in the brain may also result in neuronal loss or dysfunction through the potentiation of neurotoxins. Cognitive impairment has been associated with aging, and excess levels of cortisol in the brain. See J. R. Seckl and B. R. Walker, *Endocrinology*, 2001, 142: 1371-1376, and references cited therein. Administration of an effective amount of an 11β-HSD-1 inhibitor results in the reduction, amelioration, control or prevention of cognitive impairment associated with aging and of neuronal dysfunction. Inhibitors of 11β-HSD-1 may also be useful to treat anxiety and depression.

Atherosclerosis:

As described above, inhibition of 11β-HSD-1 activity and a reduction in the amount of cortisol are beneficial in treating or controlling hypertension. Since hypertension and dyslipidemia contribute to the development of atherosclerosis, administration of a therapeutically effective amount of an 11β-HSD-1 inhibitor of the present invention may be especially beneficial in treating, controlling, delaying the onset of or preventing atherosclerosis.

Other Utilities:

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other disorders where insulin resistance is a component.

The above diseases and conditions can be treated using the compounds of structural formula I, or the compound can be administered to prevent or reduce the risk of developing the diseases and conditions described herein. Since concurrent inhibition of 11β-HSD-2 may have deleterious side effects or may actually increase the amount of cortisol in the target tissue where reduction of cortisol is desired, selective inhibitors of 11β-HSD-1 with little or no inhibition of 11β-HSD-2 are desirable.

The 11β-HSD-1 inhibitors of structural formula I generally have an inhibition constant $IC_{50}$ of less than about 500 nM, and preferably less than about 100 nM. Generally, the $IC_{50}$ ratio for 11β-HSD-2 to 11β-HSD-1 of a compound is at least about two or more, and preferably about ten or greater. Even more preferred are compounds with an $IC_{50}$ ratio for 11β-HSD-2 to 11β-HSD-1 of about 100 or greater. For example, compounds of the present invention ideally demonstrate an inhibition constant $IC_{50}$ against 11β-HSD-2 greater than about 1000 nM, and preferably greater than 5000 nM.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to:

(a) dipeptidyl peptidase IV (DP-IV) inhibitors;

(b) insulin sensitizing agents including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin;

(c) insulin or insulin mimetics;

(d) sulfonylureas and other insulin secretagogues, such as tolbutamide, glipizide, glyburide, glimepiride, and meglitinides, such as nateglinide and repaglinide;

(e) α-glucosidase inhibitors, such as acarbose;

(f) glucagon receptor antagonists such as those disclosed in WO 98/04528, WO 99/01423, WO 00/39088 and WO 00/69810;

(g) GLP-1, GLP-1 mimetics, such as exenatide (Exendin-4) and liraglutide, and GLP-1 receptor agonists such as those disclosed in WO00/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as ezetimibe and beta-sitosterol, (v) acyl CoA:cholesterol acyltransferase inhibitors, such as, for example, avasimibe, and (vi) anti-oxidants, such as probucol;

(k) PPARδ agonists, such as those disclosed in WO97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions other than glucocorticoids, such as aspirin, non-steroidal anti-inflammatory drugs, azulfidine, and selective cyclooxygenase-2 inhibitors;

(o) protein tyrosine phosphatase 1B (PTP-1B) inhibitors;

(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and (q) glucokinase activators (GKAs).

The above combinations include a compound of structural formula I, or a pharmaceutically acceptable salt or solvate thereof, with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of structural formula I is administered orally.

The effective dosage of the active ingredient varies depending on the particular compound employed, the mode of administration, the condition being treated and the severity of the condition. Such dosages may be ascertained readily by a person skilled in the art.

When treating or preventing the diseases and conditions described herein, for which compounds of structural formula I are indicated, satisfactory results are obtained when the compounds of the invention are administered at a daily dosage of from about 0.1 to about 100 milligram per kilogram (mpk) of body weight, preferably given as a single daily dose or in divided doses about two to six times a day. The total daily dosage thus ranges from about 0.1 mg to about 1000 mg, preferably from about 1 mg to about 50 mg. In the case of a typical 70 kg adult human, the total daily dose will range from about 7 mg to about 350 mg. This dosage may be adjusted to provide the optimal therapeutic response.

Another aspect of the present invention relates to a pharmaceutical composition which comprises a compound of structural formula I, or a pharmaceutically acceptable salt or solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of structural formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of structural formula I or a salt or hydrate thereof in an amount ranging from as low as about 0.1 mg to as high as about 1.5 g, preferably from as low as about 1.0 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a flavoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants:

In vitro enzymatic activity was assessed for test compounds via a Scintillation Proximity Assay (SPA). In short, tritiated-cortisone substrate, NADPH cofactor and titrated compound were incubated with 11β-HSD-1 enzyme at 37° C. to allow conversion to cortisol to progress. Following this incubation, a preparation of protein A coated SPA beads, pre-blended with anti-cortisol monoclonal antibody and a compound of structural formula I, was added to each well. The mixture was shaken at 15° C. and was then read on a liquid scintillation counter suitable for 96 well plates. Percent inhibition was calculated relative to a non-inhibited control well and IC50 curves were generated. This assay was similarly applied to 11β-HSD-2, whereby tritiated cortisol and NAD were used as the substrate and cofactor, respectively. To begin the assay, 40 µL of substrate (25 nM 3H-Cortisone+ 1.25 mM NADPH in 50 mM HEPES Buffer, pH 7.4) was added to designated wells on a 96-well plate. The compound was dissolved in DMSO at 10 mM followed by a subsequent 50 fold dilution in DMSO. The diluted material was then titrated 4 fold, seven times. 1 µL of each titrated compound was then added in duplicate to the substrate. To start the reaction, 10 µL of 11β-HSD-1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 µL of SPA beads, pre-suspended with anti-cortisol monoclonal antibody and a compound of formula I, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1.25 nM $^3$H cortisol was added to designated single wells. 1 µL of 200 µM compound was added to each of these wells, along with 10 µL of buffer instead of enzyme. Any calculated inhibition was due to compound interfering with the cortisol binding to the antibody on the SPA beads.

Assays: Measurement of In Vivo Inhibition:

In general terms, the test compound was dosed orally to a mammal and a prescribed time interval was allowed to elapse, usually between 1 and 24 h. Tritiated cortisone was injected intravenously, followed several min later by blood collection. Steroids were extracted from the separated serum and analyzed by HPLC. The relative levels of $^3$H-cortisone and its reduction product, $^3$H-cortisol, were determined for the compound and vehicle-dosed control groups. The absolute conversion, as well as the percentage of inhibition, was calculated from these values.

More specifically, compounds were prepared for oral dosing by dissolving them in vehicle (5% hydroxypropyl-beta-cyclodextrin v/v $H_2O$, or equivalent) at the desired concentration to allow dosing at typically 10 mg per kg. Following an overnight fasting, the solutions were dosed to ICR mice (obtained from Charles River) by oral gavage, 0.5 mL per dose per animal, with three animals per test group.

After the desired time had passed, routinely either 1 or 4 h, 0.2 mL of 3 µM $^3$H-cortisone in dPBS was injected by tail vein. The animal was caged for two min followed by euthanasia in a $CO_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum, they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to $^3$H-cortisol was calculated as the ratio of AUC for cortisol over the combined AUC for cortisone and cortisol.

Preparation of Compounds of the Invention:

The compounds of structural formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the their neutral form, but the triazole moeity can be further converted into a pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electrospray ion-mass spectroscopy (ESMS).

Abbreviations Used in the Description of the Preparation of the Compounds of the Present Invention:

| AIBN | 2,2'-azobisisobutyronitrile |
|---|---|
| BOC | t-butyloxycarbonyl |
| BBr$_3$ | boron tribromide |
| 9-BBN | 9-borabicyclo[3.3.1]nonane |
| Bn | benzyl |
| nBuLi | n-butyl lithium |
| Cbz | benzyloxycarbonyl |
| CDI | 1,1'-carbonyldiimidazole |
| MeOTf | methyl trifluoromethanesulfonate |
| CH$_2$Cl$_2$ | dichloromethane |
| CH$_2$I$_2$ | diiodomethane |
| (COCl)$_2$ | oxalyl chloride |
| Cs$_2$CO$_3$ | cesium carbonate |
| DAST | (diethylamino)sulfur trifluoride |
| DMAP | 4-(dimethylamino)pyridine |
| DMF | N,N-dimethylformamide |
| Et | ethyl |
| Et$_3$N | triethylamine |
| EtOAc | ethyl acetate |
| Et$_2$Zn | diethylzinc |
| H$_2$O$_2$ | hydrogen peroxide |
| Me | methyl |
| MeCN | acetonitrile |
| MeOH | methanol |
| mCPBA | meta-chloroperbenzoic acid |
| MS | mass spectrum |
| NaBH$_4$ | sodium borohydride |
| NaHCO$_3$ | sodium hydrogencarbonate |
| NaOAc | sodium acetate |
| NBS | N-bromosuccinimide |
| Ph | phenyl |
| PyBROP | bromotripyrrolidinophosphonium hexafluorophosphate |
| PPh$_3$ | triphenylphosphine |
| pyr | pyridine |
| SOCl$_2$ | thionyl chloride |
| TFA | trifluoroacetic acid |
| TFFH | N,N,N',N'-tetramethylformamidinium hexafluorophosphate |
| THF | tetrahydrofuran |
| TLC | thin-layer chromatography |
| TsOH | p-toluenesulfonic acid |

The following reaction schemes illustrate the methods employed in the synthesis of the compounds of the present invention of structural formula I. All substituents are as defined above unless indicated otherwise.

Method A:

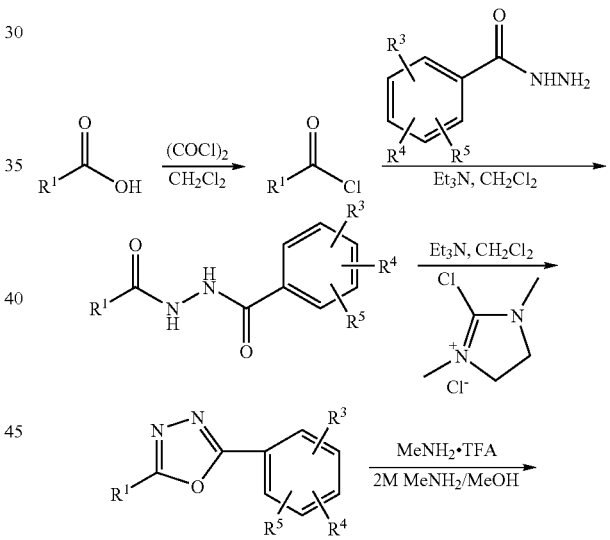

Method B:

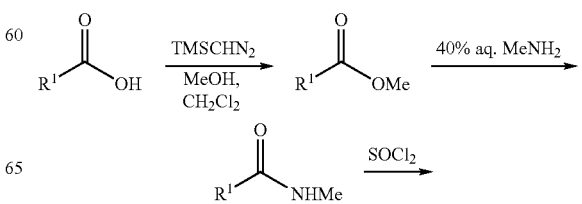

-continued
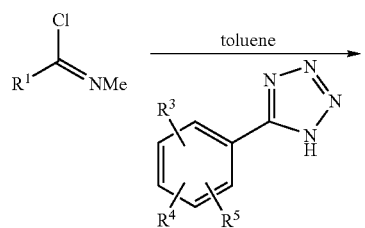
Method C:
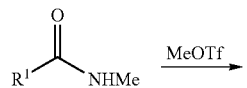
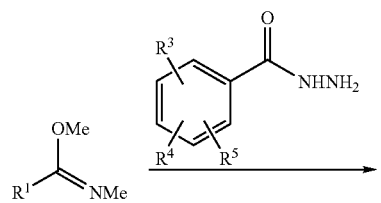
Method D:
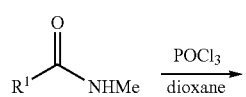
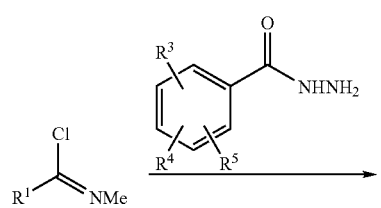
Method E:
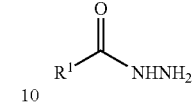
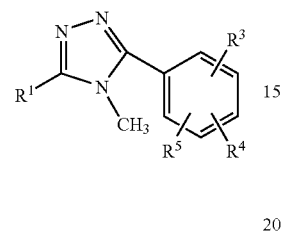
Method F:
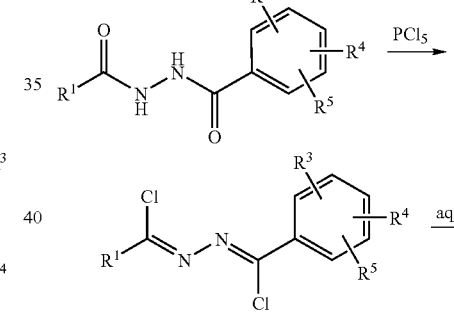
EXAMPLE 1
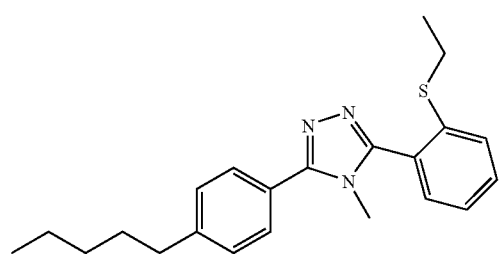

3-[2-(ethylthio)phenyl]-4-methyl-5-(4-pentylphenyl)-4H-1,2,4-triazole (1-F)

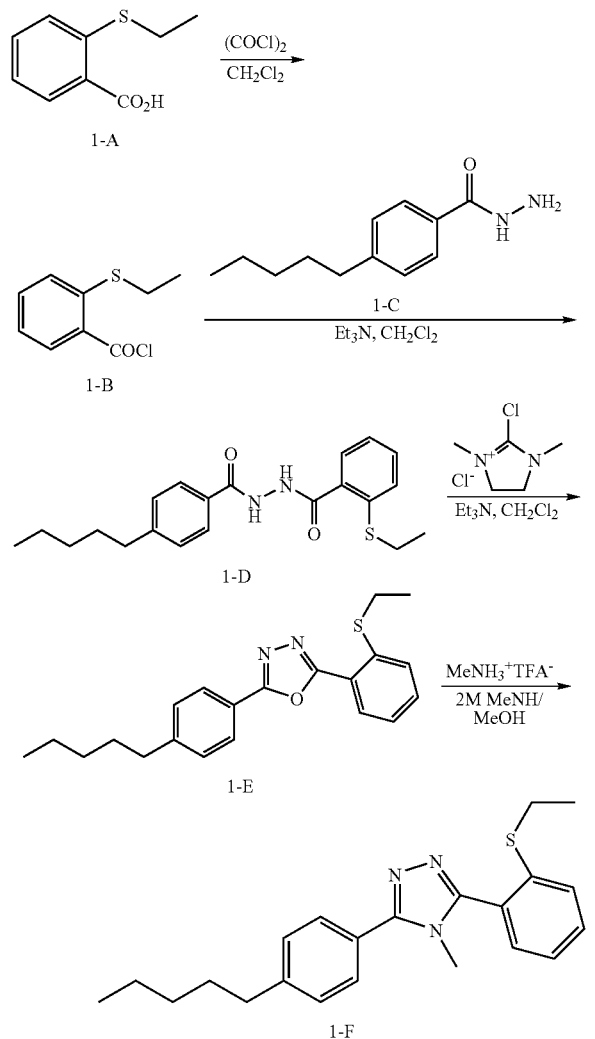

Step A:

Oxalyl chloride (113 μL, 1.3 mmol) was added slowly to a stirring suspension of 2-(ethylthio)benzoic acid (1-A) (182 mg, 1.0 mmol) and 3 μL DMF in methylene chloride (2 mL). After stirring for 3.5 h at room temperature, the mixture was concentrated in vacuo to give 2-(ethylthio)benzoyl chloride (1-B).

Step B:

To a stirring solution of 4-pentylbenzohydrazide (1-C) (206 mg, 1.0 mmol) and triethylamine (153 μL, 1.1 mmol) in methylene chloride (5 mL) was added a solution of 2-(ethylthio)benzoyl chloride (1-B) (210 mg, 1.0 mmol) in methylene chloride (2.0 mL). After stirring at room temperature for 18 h, the mixture was diluted with methylene chloride and washed with water, 10% NaHCO₃, brine, dried (MgSO₄) and evaporated in vacuo to give 2-(ethylthio)-N'-(4-pentylbenzoyl)benzohydrazide (1-D). MS m/z 371 (M+1).

Step C:

Triethylamine (735 μL, 5.28 mmol) was added to a stirring solution of 2-(ethylthio)-N'-(4-pentylbenzoyl)benzohydrazide (1-D) (326 mg, 0.88 mmol) and 2-chloro-1,3-dimethylimidazolinium chloride (448 mg, 2.64 mmol) in methylene chloride (10 mL). After stirring at room temperature for 18 h, the mixture was diluted with methylene chloride and washed with water, 1N HCl, 10% NaHCO₃, brine, dried (MgSO₄) and evaporated in vacuo. The oily residue was purified by preparative TLC (silica gel, hexane:ethyl acetate, 4:1) to provide 2-[2-(ethylthio)phenyl]-5-(4-pentylphenyl)-1,3,4-oxadiazole (1-E).

Step D:

2-[2-(Ethylthio)phenyl]-5-(4-pentylphenyl)-1,3,4-oxadiazole (1-E) (100 mg, 0.28 mmol), methylammonium trifluoroacetate (1.64 g, 11.34 mmol, prepared by combining equal amounts of methylamine and trifluoroacetic acid in ether followed by evaporation in vacuo) and methylamine (2M/MeOH, 5.68 mL, 11.34 mmol) were stirred together in a glass bomb at 150° C. for 2.5 d. The mixture was evaporated in vacuo and the residue partitioned between methylene chloride and water. The organic phase was washed with water, brine, dried (MgSO4) and concentrated in vacuo. The residue was purified by preparative TLC (silica gel, ethyl acetate:hexane, 7:3) to provide 3-[2-(ethylthio)phenyl]-4-methyl-5-(4-pentylphenyl)-4H-1,2,4-triazole (1-F). MS m/z 366 (M+1). 1H NMR (500 MHz, CDCl₃): δ 0.96 (t, 3H); 1.29 (t, 3H); 1.40 (m, 4H); 1.73, (m, 2H); 2.73, (t, 2H); 2.90 (q, 2H); 3.58 (s, 3H); 7.37 (m, 3H); 7.55 (m, 3H); 7.72, (d, 2H).

EXAMPLE 2

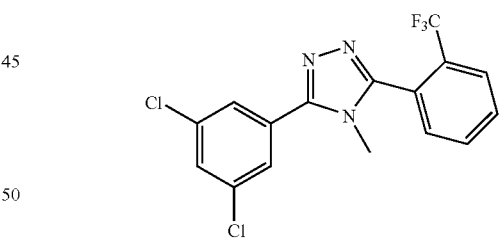

3-(3,5-dichlorophenyl)-4-methyl-5-[2-(trifluoromethyl)phenyl]-4H-1,2,4-triazole (2-F)

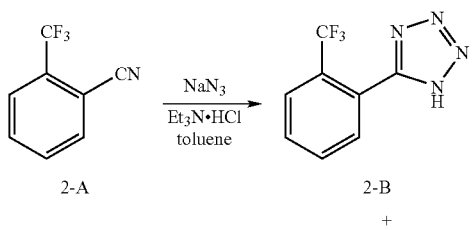

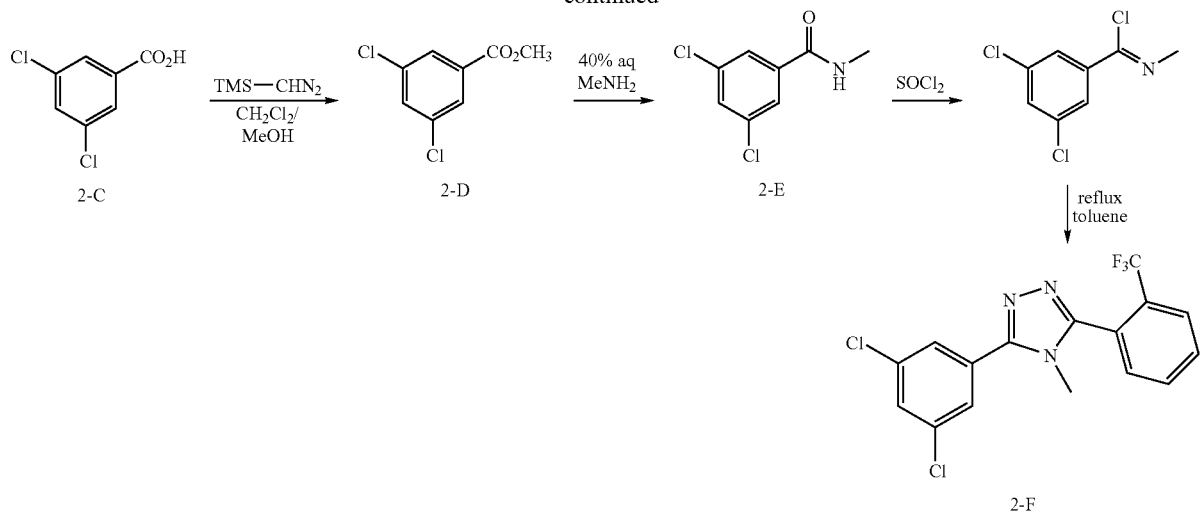

Step A:

A vigorously stirred suspension of 2-(trifluoromethyl)benzonitrile (2-A) (6.34 g, 37 mmol), sodium azide (4.81 g, 74 mmol) and triethylamine hydrochloride (10.19 g, 74 mmol) in toluene (70 mL) was heated at 110° C. for 48 h. The mixture was cooled and extracted twice with water. The combined extracts were washed with hexane and brought to pH about 1 with concentrated HCl. The precipitate which formed was filtered, washed with water and dried to give 5-[2-(trifluoromethyl)phenyl]-1H-tetrazole (2-B).

Step B:

Trimethylsilyldiazomethane (2M/ether, 3.5 mL) was added slowly to a solution of 3,5-dichlorobenzoic acid (2-C) (955 mg, 5.0 mmol) in methylene chloride (5.0 mL) and methanol (2.0 mL) until the yellow color persisted. After stirring for 10 min, the mixture was evaporated in vacuo to give methyl 3,5-dichlorobenzoate (2-D).

Step C:

Methyl 3,5-dichlorobenzoate (2-D) (1.07 g, 5.0 mmol) was suspended in a vigorously stirring solution of methylamine (40%/H$_2$O, 5.0 mL). After heating gently for 10 min, the mixture was stirred at room temperature for 18 h. The mixture was extracted with methylene chloride and the extract dried (MgSO$_4$) to provide 3,5-dichloro-N-methylbenzamide (2-E).

Step D:

Thionyl chloride (260 mL, 3.56 mmol) was added to 3,5-dichloro-N-methylbenzamide (2-E) (133 mg, 0.51 mmol) and the mixture stirred at 70° C. for 4 h and then at room temperature for 18 h. The solvent was removed under vacuum at room temperature and then at 70° C. Toluene (700 μL) was added followed by 5-[2-(trifluoromethyl)phenyl]-1H-tetrazole (2-B) (109 mg, 0.51 mmol) and the mixture stirred at 100° C. for 5 min. The mixture bubbled, cleared and was then stirred at 110° C. for 18 h. The mixture was concentrated in vacuo and the residue partitioned between methylene chloride and 10% NaHCO$_3$. The organic phase was washed with brine, dried (MgSO$_4$) and evaporated in vacuo. The residue was purified by preparative TLC (silica gel, hexane:ethyl acetate, 1:1) to provide 3-(3,5-dichlorophenyl)-4-methyl-5-[2-(trifluoromethyl)phenyl]-4H-1,2,4-triazole (2-F). MS m/z 373 (M+1); $^1$H NMR (500 MHz, CDCl$_3$): δ 3.53 (s, 3H); 7.70 (m, 2H); 7.77 (d, 2H); 7.78 (m, 2H); 7.93 (m, 1H).

EXAMPLE 3

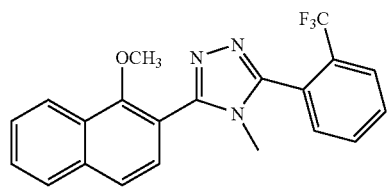

3-(1-methoxy-2-naphthyl)-4-methyl-5-[2-(trifluoromethyl)phenyl]-4H-1,2,4-triazole (3-E)

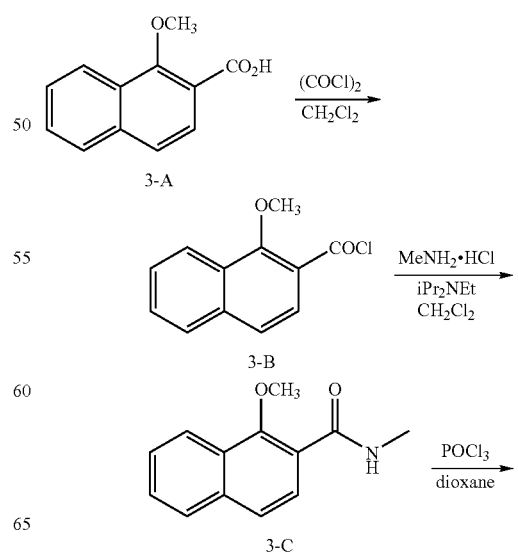

31

-continued

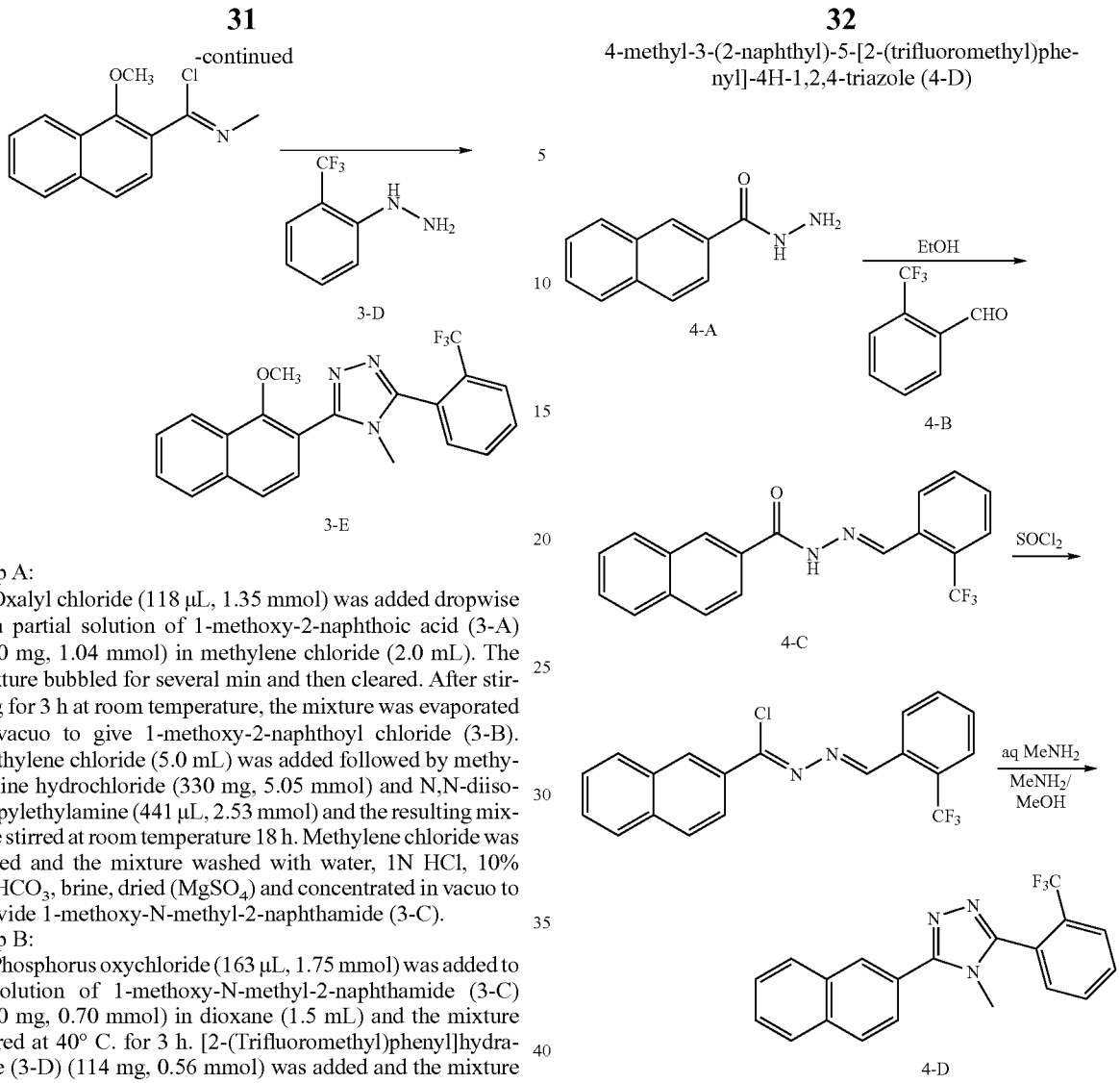

Step A:
Oxalyl chloride (118 μL, 1.35 mmol) was added dropwise to a partial solution of 1-methoxy-2-naphthoic acid (3-A) (210 mg, 1.04 mmol) in methylene chloride (2.0 mL). The mixture bubbled for several min and then cleared. After stirring for 3 h at room temperature, the mixture was evaporated in vacuo to give 1-methoxy-2-naphthoyl chloride (3-B). Methylene chloride (5.0 mL) was added followed by methylamine hydrochloride (330 mg, 5.05 mmol) and N,N-diisopropylethylamine (441 μL, 2.53 mmol) and the resulting mixture stirred at room temperature 18 h. Methylene chloride was added and the mixture washed with water, 1N HCl, 10% NaHCO$_3$, brine, dried (MgSO$_4$) and concentrated in vacuo to provide 1-methoxy-N-methyl-2-naphthamide (3-C).

Step B:
Phosphorus oxychloride (163 μL, 1.75 mmol) was added to a solution of 1-methoxy-N-methyl-2-naphthamide (3-C) (150 mg, 0.70 mmol) in dioxane (1.5 mL) and the mixture stirred at 40° C. for 3 h. [2-(Trifluoromethyl)phenyl]hydrazine (3-D) (114 mg, 0.56 mmol) was added and the mixture stirred at 40° C. for an additional 18 h. The pH was brought to about 6 with 5N NaOH and the mixture refluxed for 20 h. After cooling to room temperature and concentrating in vacuo, the residue was partitioned between methylene chloride and water. The organic phase was dried (MgSO$_4$) and evaporated in vacuo. The residue was purified by preparative TLC (silica gel, acetone:methylene chloride, 1:9) followed by reverse phase chromatography (gradient with CH$_3$CN/ H$_2$O containing 0.1% trifluoroacetic acid) to afford 3-(1-methoxy-2-naphthyl)-4-methyl-5-[2-(trifluoromethyl)phenyl]-4H-1,2,4-triazole (3-E). MS m/z 284 (M+1); $^1$H NMR (500 MHz, CDCl$_3$): δ 3.41 (s, 3H); 3.79 (s, 3H); 7.65 (m, 3H); 7.78 (m, 4H); 7.94 (m, 2H); 8.29 (m, 1H).

EXAMPLE 4

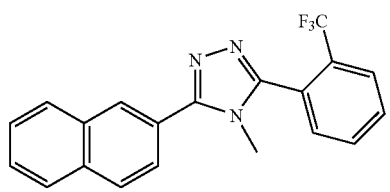

32

4-methyl-3-(2-naphthyl)-5-[2-(trifluoromethyl)phenyl]-4H-1,2,4-triazole (4-D)

Step A:
2-(Trifluoromethyl)benzaldehyde (4-B) (135 μL, 1.0 mmol) was added to a partial solution of 2-naphthohydrazide (4-A) (186 mg, 1.0 mmol) in ethanol (4 mL) at 70° C. and the mixture stirred at 70° C. for 2 h. The mixture was cooled and the thick precipitate was filtered, washed with cold ethanol and dried to give N'-{(1E)-[2-(trifluoromethyl)phenyl]-methylene}-2-naphthohydrazide (4-C).

Step B:
Thionyl chloride (1.0 mL, 13.7 mmol) was added to N'-{ (1E)-[2-(trifluoromethyl)phenyl]methylene}-2-naphthohydrazide (4-C) (171, mg, 0.5 mmol) and the suspension stirred at 75° C. for 3 h to give a clear solution. The thionyl chloride was carefully removed under vacuum at room temperature and then at 65° C. Methylamine (2M/MeOH, 2.0 mL) and aqueous methylamine (40%/H$_2$O, 1.0 mL) were added and the mixture stirred at 70° C. for 1.5 h and then at room temperature for 18 h. The mixture was diluted with water and then concentrated in vacuo to remove methanol. The residue was extracted twice with methylene chloride and the combined extracts dried (MgSO$_4$) and evaporated in vacuo. The residue was purified by preparative TLC (silica gel, isopropanol:hexane, 1:4) to afford 4-methyl-3-(2-naphthyl)-5-[2-(trifluoromethyl)phenyl]-4H-1,2,4-triazole (4-D). MS m/z 354 (M+1); $^1$H NMR (500 MHz, CDCl$_3$): δ 3.59 (s, 3H); 7.65 (m, 3H); 7.77 (m, 2H); 7.95, (m, 4H); 8.05 (d, 1H); 8.28 (s, 1H).

EXAMPLE 5

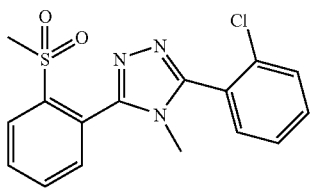

3-(2-chlorophenyl)-4-methyl-5-[2-(methylsulfonyl) phenyl]-4H-1,2,4-triazole (5-D)

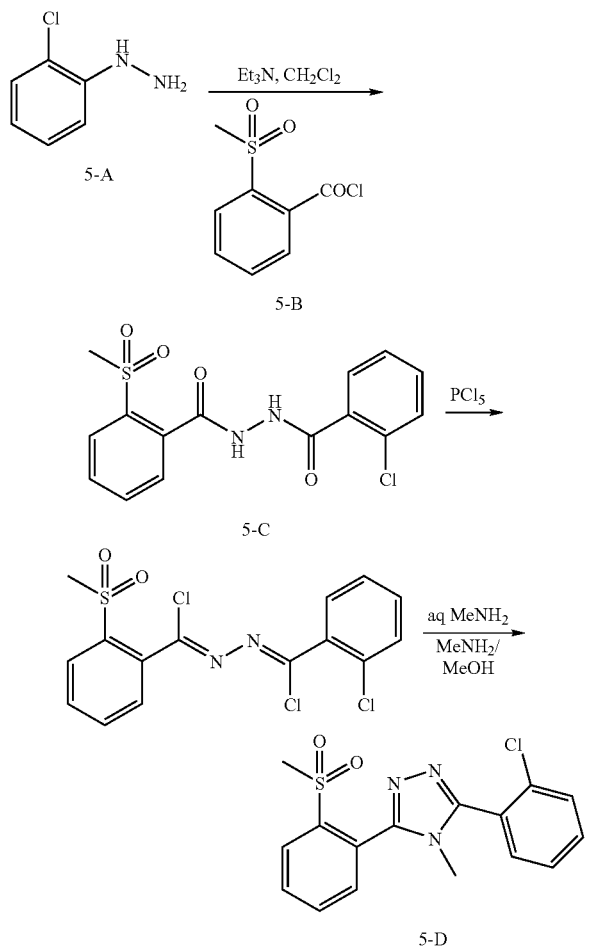

Step A:

A solution of 2-(methylsulfonyl)benzoyl chloride (5-B) (436 mg, 2.0 mmol) in methylene chloride (2.0 mL) was added slowly to a solution of (2-chlorophenyl)hydrazine (5-A) (342 mg, 2.0 mmol) and triethylamine (279 μL, 2.0 mmol) in methylene chloride (10 mL) at 0° C. After stirring at room temperature for 2 h, the mixture was extracted with 1N HCl, 10% NaHCO$_3$, dried (MgSO$_4$) and evaporated in vacuo to give 2-chloro-N'-[2-(methylsulfonyl)benzoyl]benzohydrazide (5-C). MS m/z 353 (M+1).

Step B:

Phosphorus pentachloride (201 mg, 0.98 mmol) was added to 2-chloro-N'-[2-(methylsulfonyl)benzoyl]benzohydrazide (5-C) (292 mg, 0.83 mmol) and the mixture stirred at 125° C. for 30 min during which time, after gas evolution, the solid formed a melt. The mixture was evaporated under diminished pressure at room temperature (15 min) and at 125° C. (10 min). After cooling to room temperature, methylamine (40%/H$_2$O) was added and the mixture stirred at 125° C. for 15 min. After cooling again, methylamine (2M/MeOH) was added and the mixture stirred for 2 h at 125° C. The mixture was cooled, diluted with water and concentrated in vacuo. The residue was extracted three times with methylene chloride and the combined extracts dried (MgSO$_4$) and evaporated in vacuo. The residue was purified by preparative TLC (silica gel, methanol:methylene chloride, 5:95) to provide 3-(2-chlorophenyl)-4-methyl-5-[2-(methylsulfonyl)phenyl]-4H-1,2,4-triazole (5-D). MS m/z 335 (M+1); $^1$H NMR (500 MHz, CDCl$_3$): δ 3.30 (s, 3H); 3.37 (s, 3H); 7.53 (m, 5H); 7.85 (m, 2H); 8.32 (dd, 1H).

EXAMPLE 6

4-[4-methyl-5-(1-methyl-1H-indol-4-yl)-4H-1,2,4-triazol-3-yl]phenol (6-C)

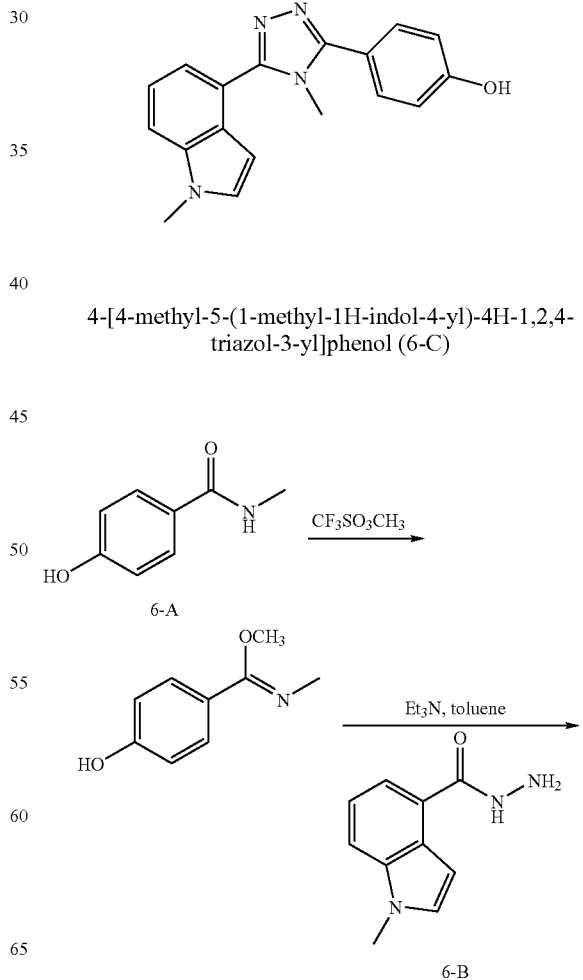

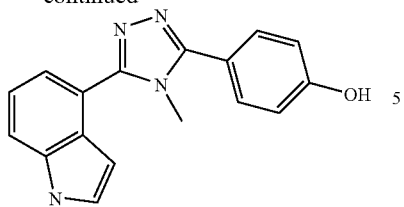

6-C

Methyl trifluoromethanesulfonate (200 μL, 1.76 mmol) was added to 4-hydroxy-N-methylbenzamide (6-A) (133 mg, 0.881 mmol) and the mixture stirred at 65° C. for 10 min. Toluene (0.6 mL) was added and the suspension stirred rapidly at 65° C. for 30 min. Toluene (0.4 mL), triethylamine (370 μL, 2.67 mmol) and a solution of 1-methyl-1H-indole-4-carbohydrazide (6-B) (100 mg, 0.528 mmol) in toluene (1.0 mL) and DMF (250 μL) were added and the mixture stirred at 65° C. for 3 h and then at 125° C. for 18 h. The mixture was evaporated in vacuo and the residue purified by preparative TLC (silica gel, methylene chloride:methanol, 95:5) to provide 4-[4-methyl-5-(1-methyl-1H-indol-4-yl)-4H-1,2,4-triazol-3-yl]phenol (6-C). $^1$H NMR (500 MHz, CD$_3$OD): δ 3.63 (s, 3H); 3.92 (s, 3H); 6.53 (d, 1H); 7.00 (d, 2H); 7.37 (m, 3H); 7.64, (m, 3H).

The following additional examples were prepared using one of Methods A-F and following the specific conditions detailed for Examples 1-6:

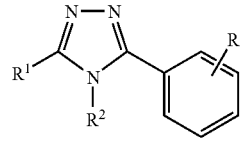

| R$^1$ | R$^2$ | R | Mass Spec | Method |
|---|---|---|---|---|
| 5-(2-Cl-phenyl)-1-Me pyrazol-3-yl | Me | 2-Cl | 384 | A |
| 1-Methyl-1H-indol-4-yl* | Me | 4-OH | | C |
| 1-Methyl-1H-indo-4-yl* | Me | 2-MeO | | A |
| 1,2,3-tri-Me-1H-indol-5-yl* | Me | 4-OH | | C |
| 1-Me-1H-indol-4-yl* | Me | 2-Cl | | A |
| 1-Me-1H-indol-4-yl* | Me | 2-CF$_3$ | | A |
| 2,4-di-Cl-phenyl | Me | 2-CF$_3$ | 372 (M + 1) | D |
| 2-Me-naphth-1-yl | Me | 2-CF$_3$ | 368 (M + 1) | A |
| 1-F-naphth-2-yl | Me | 2-CF$_3$ | 372 (M + 1) | A |
| 1-Methylamino-naphth-2-yl | Me | 2-CF$_3$ | 383 (M + 1) | A |
| 2,4-di-CF$_3$-phenyl | Me | 2-CF$_3$ | 440 (M + 1) | A |
| 2,4-di-Me-phenyl | Me | 2,4-di-Me | 292 (M + 1) | D |
| 2,4-di-Cl-phenyl | Me | 2-Cl | 240 (M + 2) | E |
| 2-Cl-4-F-phenyl | Me | 2-CF$_3$ | 356 (M + 1) | B |
| 2,4-di-Cl-phenyl | Me | 2-MeS | 350 (M + 1) | D |
| 2,4-di-Cl-phenyl | Me | 2-Me | 318 (M + 1) | D |
| 2,4-di-Cl-phenyl | Me | 2-EtS | 364 (M + 1) | D |
| 1-MeO-7-Cl-naphth-2-yl | Me | 2-CF$_3$ | 418 (M + 1) | D |
| 2-MeS-4-CF$_3$-phenyl | Me | 2-CF$_3$ | 418 (M + 1) | D |
| 1-MeO-naphth-2-yl | Me | 2-CF$_3$ | 284 (M + 1) | D |
| 2-CF$_3$-phenyl | Me | 2-CF$_3$ | 372 (M + 1) | E |
| 2,5-di-Cl-phenyl | Me | 2-CF$_3$ | 372 | D |
| 1-MeO-4-Cl-naphth-2-yl | Me | 2-CF$_3$ | 418 (M + 1) | D |
| 2-Cl-4-EtS-phenyl | Me | 2-F | 348 (M + 1) | D |
| 2,4-di-Cl-phenyl | Me | 2-cyclopropyl | 344 (M + 1) | D |
| 2-MeO-phenyl | Me | 2-CF$_3$ | 334 (M + 1) | E |
| 2,6-di-Cl-phenyl | Me | 2-CF$_3$ | 372 (M + 1) | E |
| 2-CF$_3$O-phenyl | Me | 2-CF$_3$ | 388 (M + 1) | E |
| 2-Cl-phenyl | Me | 2-Cl,4-F— | 322 (M + 1) | E |
| 2-Cl-phenyl | Me | 2-CHF$_2$O | 336 (M + 1) | E |
| 4-(n-pentyl)-phenyl | Me | 2-CF$_3$ | 374 (M + 1) | E |
| 2-(phenoxy)-phenyl | Me | 2-CF$_3$ | 396 (M + 1) | B |
| 2-CF$_3$-phenyl | Me | 2-(prop-2-yn-1-yloxy) | 358 (M + 1) | E |
| 2,4-di-Cl-phenyl | Me | 2-CHF$_2$O | 372 (M + 1) | E |
| 2-[(4-Cl-phenyl)thio]phenyl | Me | 2-CF$_3$ | 445 (M + 1) | E |
| 2-(n-propyloxy)phenyl | Me | 2-CF$_3$ | 362 (M + 1) | E |
| 2-Cl-phenyl | Me | 2-Cl | 304 | E |
| 2-EtO-phenyl | Me | 2-CF$_3$ | 348 (M + 1) | E |
| 2-Br-phenyl | Me | 2-CF$_3$ | 331 (M + 1) | E |
| 2-Cl-phenyl | Me | 2-CF$_3$ | 338 (M + 1) | E |
| 2,3-di-Cl-phenyl* | Me | 2,3-di-Cl | | |
| 4-Cl-5-(2-Cl-phenyl)-1-Me-pyrazol-4-yl | Me | 2-CF$_3$ | 452 | A |
| 2,4,6-tri-Cl-naphth-1-yl | Me | 2-CF$_3$ | 458 (M + 2) | F |
| 4-(n-pentyl)-phenyl | Me | 2-Cl | 340 (M + 1) | E |
| 4-(n-pentyl)-phenyl | Me | 2-MeSO$_2$ | 384 (M + 1) | A |
| 5-Cl-6-MeO-naphth-1-yl | Me | 2-CF$_3$ | | F |
| 3-Cl-naphth-2-yl | Me | 2-CF$_3$ | 388 (M + 1) | E |
| 4-(4-Cl-phenoxy)phenyl | Me | 2-CF$_3$ | 430 (M + 1) | E |
| 2-(4-Cl-phenoxy)phenyl | Me | 2-CF$_3$ | 430 (M + 1) | E |
| 2-Me-phenyl | Me | 2-CF$_3$O | 334 (M + 1) | E |
| 2-Me-phenyl | Me | 2-Br | 330 (M + 2) | E |
| 2-Me-phenyl | Me | 2,3-di-Cl | 318 | E |
| 2-MeO-phenyl | Me | 2-Br | 346 (M + 2) | E |
| 2-MeO-phenyl | Me | 2,3-di-Cl | 336 (M + 2) | E |
| 2-Cl-phenyl | Me | 2-CF$_3$O | 354 (M + 1) | E |
| 2-Cl-phenyl | Me | 2-Br | 350 (M + 2) | E |
| 2-Cl-phenyl | Me | 2,3-di-Cl | 340 (M + 2) | E |
| 2-Cl-phenyl | Me | 2-Cl,3-CF$_3$ | 372 | E |
| 2-(4-F-phenoxy)phenyl | Me | 2-CF$_3$ | 630 (M + 1) | E |
| 3-MeO-4-Cl-naphth-2-yl | Me | 2-CF$_3$ | 418 (M + 1) | E |
| 2-(4-Cl-phenoxy)phenyl | Me | 2-MeS | 408 (M + 1) | E |
| 2-(4-Cl-phenoxy)phenyl | Me | 2-MeSO$_2$ | 430 (M + 1) | E |
| 2-Cl-phenyl | Cyclopropyl | 2-CF$_3$ | 364 (M + 1) | B |

*characterized by means of 500 MHz NMR spectroscopy.

Example of a Pharmaceutical Formulation

As a specific embodiment of an oral composition of a compound of the present invention, 50 mg of any of Examples 1-6 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by

What is claimed is:

1. A compound of structural formula II:

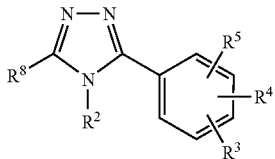

or a pharmaceutically acceptable salt thereof; wherein
each n is 0, 1, or 2;
each p is 0, 1, or 2;
$R^8$ is naphthyl or heteroaryl wherein heteroaryl is selected from the group consisting of
pyridyl,
thienyl,
furyl,
pyrazolyl,
thiazolyl,
oxazolyl,
imidazolyl,
indolyl,
benzothiophenyl,
benzofuryl, and
benzimidazolyl;
in which naphthyl and heteroaryl are substituted with one to three substituents independently selected from $R^3$, $R^4$, and $R^5$;
$R^2$ is methyl or cyclopropyl;
$R^3$, $R^4$, and $R^5$ are each independently selected from the group consisting of
hydrogen,
formyl,
$C_{1-6}$ alkyl,
$C_{2-6}$ alkenyl,
$(CH_2)_n$-aryl,
$(CH_2)_n$-heteroaryl,
$(CH_2)_n$-heterocyclyl,
$(CH_2)_n C_{3-7}$ cycloalkyl,
halogen,
$OR^7$,
$(CH_2)_n N(R^7)_2$,
cyano,
$(CH_2)_n CO_2 R^7$,
$NO_2$,
$(CH_2)_n NR^7 SO_2 R^6$,
$(CH_2)_n SO_2 N(R^7)_2$,
$(CH_2)_n S(O)_p R^6$,
$(CH_2)_n SO_2 OR^7$,
$(CH_2)_n NR^7 C(O)N(R^7)_2$,
$(CH_2)_n C(O)N(R^7)_2$,
$(CH_2)_n NR^6 C(O)R^6$,
$(CH_2)_n NR^6 CO_2 R^7$,
$O(CH_2)_n C(O)N(R^7)_2$,
$CF_3$,
$CH_2 CF_3$,
$OCF_3$,
$OCHCF_2$, and
$OCH_2 CF_3$;
wherein aryl, heteroaryl, cycloalkyl, and heterocyclyl are unsubstituted or substituted with one to three substituents independently selected from halogen, hydroxy, $C_{1-4}$ alkyl, trifluoromethyl, trifluoromethoxy, and $C_{1-4}$ alkoxy; and wherein any methylene ($CH_2$) carbon atom in $R^3$, $R^4$, and $R^5$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;
each $R^6$ is independently selected from the group consisting of
$C_{1-8}$ alkyl,
$(CH_2)_n$-aryl,
$(CH_2)_n$-heteroaryl, and
$(CH_2)_n C_{3-7}$ cycloalkyl;
wherein alkyl and cycloalkyl are unsubstituted or substituted with one to five substituents independently selected from halogen, oxo, $C_{1-4}$ alkoxy, $C_{1-4}$ alkylthio, hydroxy, amino; and aryl and heteroaryl are unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy;
or two $R^6$ groups together with the atom to which they are attached form a 5- to 8-membered mono- or bicyclic ring system optionally containing an additional heteroatom selected from O, S, and $NC_{1-4}$ alkyl; and
each $R^7$ is hydrogen or $R^6$.

2. The compound of claim 1 wherein $R^2$ is methyl.
3. The compound of claim 1 wherein $R^8$ is indolyl or pyrazolyl substituted with one to three substituents independently selected from $R^3$.
4. The compound of claim 3 wherein $R^2$ is methyl.
5. A compound which is selected from the group consisting of:
4-methyl-3,5-bis[2-(trifluoromethyl)phenyl]-4H-1,2,4-triazole;
4-methyl-3-[4-(methylthio)-2-(trifluoromethyl)phenyl]-5-[2-(trifluoromethyl)phenyl]-4H-1,2,4-triazole;
4-methyl-3-(4-pentylphenyl)-5-[2-(trifluoromethyl)phenyl]-4H-1,2,4-triazole;
3-(2-chlorophenyl)-4-methyl-5-[2-(trifluoromethyl)phenyl]-4H-1,2,4-triazole;
3-(1-methoxy-2-naphthyl)-4-methyl-5-[2-(trifluoromethyl)phenyl]-4H-1,2,4-triazole;
4-[5-(2-chlorophenyl)-4-methyl-4H-1,2,4-triazol-3-yl]-1-methyl-1H-indole;
4-{4-methyl-5-[2-(trifluoromethyl)phenyl]-4H-1,2,4-triazol-3-yl}-1-methyl-1H-indole;
3-(2-bromophenyl)-4-methyl-5-[2-(trifluoromethyl)phenyl]-4H-1,2,4-triazole;
3-(7-chloro-1-methoxy-2-naphthyl)-4-methyl-5-[2-(trifluoromethyl)-4H-1,2,4-triazole;
4-[4-methyl-5-(1-methyl-1H-indol-4-yl)-4H-1,2,4-triazol-3-yl]phenol;
3-(2,4-dichlorophenyl)-4-methyl-5-[2-(trifluoromethyl)phenyl]-4H-1,2,4-triazole;
3-[2,4-bis(trifluoromethyl)phenyl]-4-methyl-5-[2-(trifluoromethyl)phenyl]-4H-1,2,4-triazole;
3-(2-chlorophenyl)-5-(2,4-dichlorophenyl)-4-methyl-4H-1,2,4-triazole;
3-(2-chloro-4-fluorophenyl)-4-methyl-5-[2-(trifluoromethyl)phenyl]-4H-1,2,4-triazole;
3-(2,4-dichlorophenyl)-4-methyl-5-[2-(methylthio)phenyl]-4H-1,2,4-triazole;
3-(2,4-dichlorophenyl)-4-methyl-5-(2-methylphenyl)-4H-1,2,4-triazole;

3-(2-chlorophenyl)-5-[5-(2-chlorophenyl)-1-methyl-1H-pyrazol-3-yl]-4-methyl-4H-1,2,4-triazole;
4-[5-(2-methoxyphenyl)-4-methyl-4H-1,2,4-triazol-3-yl]-1-methyl-1H-indole;
4-methyl-3-(2-methyl-1-naphthyl)-5-[2-(trifluoromethyl)phenyl]-4-methyl-4H-1,2,4-triazole;
3-(1,4-dichloro-2-naphthyl)-4-methyl-5-[2-(trifluoromethyl)phenyl]-4H-1,2,4-triazole;
3-(4-chloro-1-methoxy-2-naphthyl)-4-methyl-5-[2-(trifluoromethyl)phenyl]-4H-1,2,4-triazole;
3-(1-fluoro-2-naphthyl)-4-methyl-5-[2-(trifluoromethyl)phenyl]-4H-1,2,4-triazole;
N-methyl-2-{4-methyl-5-(trifluoromethyl)phenyl]-4H-1,2,4-triazol-3-yl}naphthalen-1-amine;
3,5-bis-(2,4-dimethylphenyl)-4-methyl-4H-1,2,4-triazole;
3-(2,4-dichlorophenyl)-5-[2-(ethylthio)phenyl]-4-methyl-4H-1,2,4-triazole;
3-(2-cyclopropylphenyl)-5-(2,4-dichlorophenyl)-4-methyl-4H-1,2,4-triazole;
3-[(2-chloro-4-(ethylthio)phenyl)]-5-(2-fluorophenyl)-4-methyl-4H-1,2,4-triazole;
3-(2-methoxyphenyl)-4-methyl-5-[2-(trifluoromethyl)phenyl]-4H-1,2,4-triazole;
3-(2,6-dichlorophenyl)-4-methyl-5-[2-(trifluoromethyl)phenyl]-4H-1,2,4-triazole;
3-(2-chlorophenyl)-5-[(2-difluoromethoxy)phenyl]-4-methyl-4H-1,2,4-triazole;
3-(2-chloro-4-fluorophenyl)-5-(2-chlorophenyl)-4-methyl-4H-1,2,4-triazole;
3-(2,4-dichlorophenyl)-5-[(2-difluoromethoxy)phenyl]-4-methyl-4H-1,2,4-triazole;
4-methyl-3-(2-phenoxyphenyl)-5-[2-(trifluoromethyl)phenyl]-4H-1,2,4-triazole;
4-methyl-3-[2-(trifluoromethoxy)phenyl]-5-[2-(trifluoromethyl)phenyl]-4H-1,2,4-triazole;
4-methyl-3-[2-(prop-2-yn-1-yloxy)phenyl]-5-[2-(trifluoromethyl)phenyl]-4H-1,2,4-triazole;
3-{2-[(4-chlorophenyl)thio]phenyl}-4-methyl-5-[2-(trifluoromethyl)phenyl]-4H-1,2,4-triazole;
3-[2-(difluoromethoxy)phenyl]-4-methyl-5-[2-(trifluoromethyl)phenyl]-4H-1,2,4-triazole;
3-(2-ethoxyphenyl)-4-methyl-5-[2-(trifluoromethyl)phenyl]-4H-1,2,4-triazole;
4-methyl-3-(2-propoxyphenyl)-5-[2-(trifluoromethyl)phenyl]-4H-1,2,4-triazole;
3,5-bis(2-chlorophenyl)-4-methyl-4H-1,2,4-triazole;
3,5-bis(2,3-dichlorophenyl)-4-methyl-4H-1,2,4-triazole;
3-(3-chloro-2-naphthyl)-4-methyl-5-[2-(trifluoromethyl)phenyl]-4H-1,2,4-triazole;
3-(5-chloro-6-methoxy-1-naphthyl)-4-methyl-5-[2-(trifluoromethyl)phenyl]-4H-1,2,4-triazole;
3-[2-(4-chlorophenoxy)phenyl]-4-methyl-5-[2-(trifluoromethyl)phenyl]-4H-1,2,4-triazole;
3-[4-(4-chlorophenoxy)phenyl]-4-methyl-5-[2-(trifluoromethyl)phenyl]-4H-1,2,4-triazole;
3-[4-chloro-5-(2-chlorophenyl)-1-methyl-1H-pyrazol-3-yl]-4-methyl-5-[2-(trifluoromethyl)phenyl]-4H-1,2,4-triazole;
4-methyl-3-(2,4,6-trichloro-1-naphthyl)-5-[2-(trifluoromethyl)phenyl]-4H-1,2,4-triazole;
3-(2-chlorophenyl)-4-methyl-5-[2-(trifluoromethoxy)phenyl]-4H-1,2,4-triazole;
3-(2-bromophenyl)-5-(2-methoxyphenyl)-4-methyl-4H-1,2,4-triazole;
3-(2,3-dichlorophenyl)-4-methyl-5-(2-methylphenyl)-4H-1,2,4-triazole;
3-(2,3-dichlorophenyl)-5-(2-methoxyphenyl)-4-methyl-4H-1,2,4-triazole;
3-(2-bromophenyl)-4-methyl-5-(2-methylphenyl)-4H-1,2,4-triazole;
4-methyl-3-(2-methylphenyl)-5-[2-(trifluoromethoxyl)phenyl]-4H-1,2,4-triazole;
3-(2-chlorophenyl)-4-cyclopropyl-5-[(2-(trifluoromethyl)phenyl]-4H-1,2,4-triazole;
3-(4-chloro-3-methoxy-2-naphthyl)-4-methyl-5-[(2-(methylthio)phenyl]-4H-1,2,4-triazole;
3-[2-(4-chlorophenoxy)phenyl]-4-methyl-5-[(2-(methylthio)phenyl]-4H-1,2,4-triazole;
3-[2-(4-chlorophenoxy)phenyl]-4-methyl-5-[(2-(methylsulfonyl)phenyl]-4H-1,2,4-triazole;
3-(2-chlorophenyl)-5-(2,3-dichlorophenyl)-4-methyl-4H-1,2,4-triazole;
3-(2-bromophenyl)-5-(2-chlorophenyl)-4-methyl-4H-1,2,4-triazole;
3-[2-(4-fluorophenoxy)phenyl]-4-methyl-5-[2-(trifluoromethyl)phenyl]-4H-1,2,4-triazole;
3-(2-chlorophenyl)-5-[2-chloro-3-(trifluoromethyl)phenyl]-4-methyl-4H-1,2,4-triazole; and
4-[4-methyl-5-(1,2,3-trimethyl-1H-indol-5-yl)-4H-1,2,4-triazol-3-yl]phenol;
or a pharmaceutically acceptable salt thereof.

* * * * *